United States Patent [19]

Keller et al.

[11] 4,310,312
[45] Jan. 12, 1982

[54] ANTERIOR TOOTH PROSTHESIS

[76] Inventors: Ronald P. Keller, 5431 Alwood Forest, St. Louis, Mo. 63128; William G. Keller, 2107 Briargate La., Kirkwood, Mo. 63122

[21] Appl. No.: 158,244

[22] Filed: Jun. 10, 1980

[51] Int. Cl.³ .............................................. A61C 0/00
[52] U.S. Cl. .................... 433/204; 433/180
[58] Field of Search ............... 433/208, 206, 204, 180, 433/172

[56] References Cited

U.S. PATENT DOCUMENTS

| Re. 16,876 | 2/1928 | Poston | 433/204 |
| 1,678,779 | 9/1958 | Kile | 433/204 |
| 3,004,343 | 10/1961 | Rydin | 433/202 |

OTHER PUBLICATIONS

Journal of Prosthetic Dentistry, vol. 37, No. 1, Jan. 1977, pp. 28–31.

Primary Examiner—Robert Peshock
Attorney, Agent, or Firm—Polster, Polster and Lucchesi

[57] ABSTRACT

An anterior tooth prosthesis has a one-piece metal framework with laterally extending wings, a central saddle with a concave surface and a peg integral with the surface, and a plastic pontic having a peg-receiving mortise in which the peg is seated and secured.

3 Claims, 7 Drawing Figures

ANTERIOR TOOTH PROSTHESIS

BACKGROUND OF THE INVENTION

Frequently a front (anterior) tooth is lost in an accident or missing due to a congenital defect, leaving sound abutment teeth. Conventional full coverage reduction requires preparation of abutment teeth by grinding them down and fitting a cap. This is not only expensive and uncomfortable for the patient, but degrades the abutment teeth. The use of an orthodontic arch wire requires that a slot be drilled in the sound abutment teeth and the space between the bar-supported pontic and the abutment teeth be filled with composite resin. A description of such an approach is to be found in JADA Volume 100, Feb. 1980, pages 198-202. Removable partials tend to be bulky, expensive, and traumatic to gingival tissue, and can torque the abutment teeth to loosen them.

It has been proposed to attach a cast fixed prosthesis to abutment teeth using a composite resin and acid-etch procedure without reducing the abutment teeth (see J. Prosthet. Dent., Jan. 1977, pages 28–31; Quintessence International 7/1979, pages 23 et seq., Restorative Dentistry, Endodontics Number 7, Report 1772, July 1979, pages 1–7). The pontic itself was porcelain, formed around a narrow bridging bar between perforated wings.

One of the objects of this invention is to provide a prosthesis of the winged, cast, fixed type utilizing the acid-etch technique and composite resin system, which is less expensive and more esthetically acceptable and versatile than the prosthesis using porcelain pontics.

Other objects will occur to those skilled in the art in light of the following description and accompanying drawings.

SUMMARY OF THE INVENTION

In accordance with this invention, generally stated, an anterior tooth prosthesis is provided that comprises a one-piece metal framework having laterally extending wings, a central saddle with a concave surface and a peg integral with the surface and projecting therefrom, and a plastic pontic with a peg-receiving mortise in which the peg is seated and secured. The pontic is preferably acrylic, and has a filled, formed part extending toward the gum line.

BRIEF DESCRIPTION OF THE DRAWINGS

Figure 6:
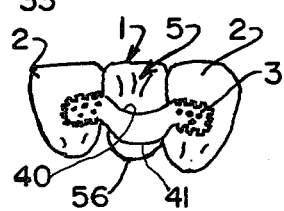
FIG. 6 is a view in rear elevation of the prosthesis anchored to sound abutment teeth.
Figure 7:
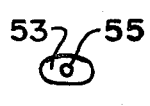
FIG. 7 is a bottom plan view of a preformed body part of a pontic.

Referring now to the drawing for one illustrative embodiment of this invention, reference numeral 1 indicates an anterior tooth fixed partial denture (prosthesis) which, in FIG. 6, is shown as anchored to sound abutment teeth 2.

The prosthesis 1 is made up of a one-piece metal framework 3 and a pontic 5.

The framework 3 has wings 30 and 31, the edges of which are provided with crenellations 32 and the flat surfaces of which are provided with retentive holes 33, and a central saddle 34, with a convex surface 35 and a concave surface 36. The surface 36 is broad, and defines a rounded end part 41 and a relatively wide, shallow U-shaped mouth 40, which, when the prosthesis is in place, is directed away from the gum immediately adjacent the rounded end part 41. A peg 37, integral with and projecting from the concave surface 36, has a root 38 at which it meets the concave surface 36 toward the mouth 40, and a free end 39. The peg 37 can be tapered convergently toward its free end 39.

Figure 1:
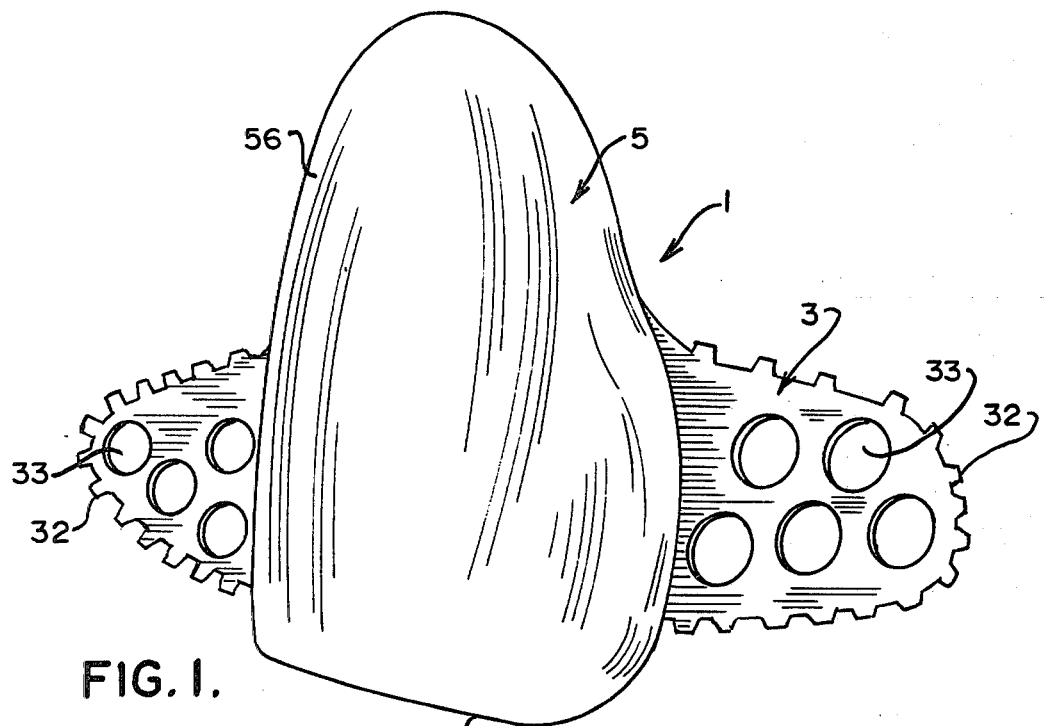
FIG. 1 is an enlarged view in perspective of one illustrative embodiment of prosthesis of this invention.
Figure 2:
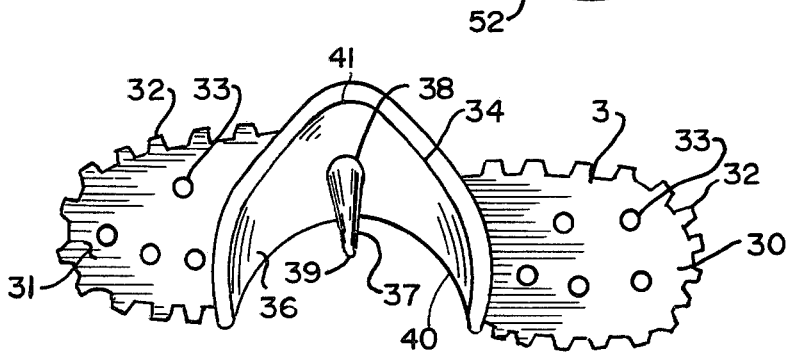
FIG. 2 is a view in front elevation, in the orientation of FIG. 1, of a metal framework component of the prosthesis of FIG. 1.
Figure 3:
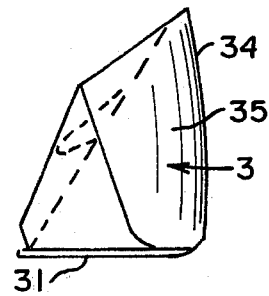
FIG. 3 is a view in side elevation.
Figure 4:
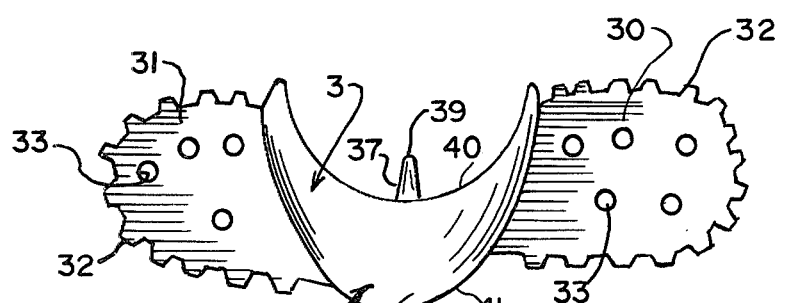
FIG. 4 is a view in rear elevation.
Figure 5:
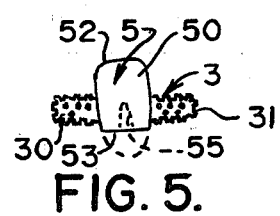
FIG. 5 is a view in front elevation, only slightly enlarged from conventional size, of the prosthesis in one stage of manufacture.

As shown particularly in FIG. 5, the pontic 5 has a preformed body part 50. The body part 50 has a bite edge 52 projecting beyond the mouth 40 of the saddle, and a mounting end surface 53, through which a mortise 55 opens. The pontic has a filled and formed part 56, secured to the mounting end surface 53 and extending to the gum line. The part 56 of the pontic is preferably made of the same material as the preformed body part so as to form effectively a continuous, unitary pontic.

Acrylic denture teeth are standard articles of commerce. They come in various sizes, shapes, and shades of color. They are ground to fit by dental laboratories, or, in some cases, by dentists. In making the prosthesis of this invention, preferably full arch impressions of both arches are taken and a bite registration is made. An appropriate tooth shade is selected. The metal framework is cast, with the elements described, in a configuration and to dimensions determined by the impression. The tooth is ground to fit, with a substantially flat mounting end surface, and a mortise is drilled from the mounting surface toward but short of the bite edge of the tooth. This preformed body part is then securely fixed to the peg with acrylic cement ("composite") and composite constituting the filled and formed gum part is molded to the mounting end surface, bonding to the surface and forming effectively a unitary pontic. With the usual finishing, the prosthesis is complete.

The completed prosthesis is then tried in and a definite seat obtained. The surfaces of the abutment teeth to be covered are acid-etched. Unfilled resin is mixed and applied to the etched enamel surface. Filled resin is then mixed and applied to the internal surface of the wings, completely filling the retentive holes. The prosthesis is seated and held firmly in place, preferably with the aid of a stone matrix. The excess resin will be squeezed through the retentative holes. Retention can be enchanced by allowing a small amount of resin to overlap the crenellations at the margins of the wings.

On maxillary anteriors a 1 mm clearance is necessary on the abutments for the prosthesis as supplied commercially. A slight reduction may be necessary on either the abutments or the opposing dentention. However, it is apparent that in situations in which the prosthesis of this invention can be used, no radical preparation is required.

It is also apparent that there are certain specific contraindications, such as mobile abutment teeth, insufficient enamel surface for bonding, occlusal stops on the lingual surfaces of abutment teeth, anterior protected occlusion functioning on the wings, or severly rotated abutment teeth, but these are not the norm.

Numerous variations in the construction of the prosthesis of this invention, within the scope of the appended claims, will occur to those skilled in the art in the light of the foregoing disclosure. For example, multiple missing teeth could be replaced using a single prosthesis with multiple pontics, additional retentive wings could be added to the prosthesis, a lingual arm attached to the pontic further from the wings could be used to maintain a natural diastema, or when the missing tooth is adjacent to a posterior tooth the posterior wing of the prosthesis could be replaced by an occlusal rest.

Having thus described the invention, what is claimed and desired to be secured by Letters Patent is:

1. An anterior tooth prosthesis comprising a one-piece metal framework having laterally extending wings, a central saddle with a broad concave surface defining a mouth at an edge away from the gum adjacent the framework when the prosthesis is in place, and a peg integral with said surface and projecting toward said mouth, and a plastic pontic having a peg-receiving mortise in which said peg is seated and secured and a bite edge projecting beyond said mouth of said saddle.

2. The prosthesis of claim 1 wherein the pontic is acrylic.

3. The prosthesis of claims 1 or 2 wherein said pontic has a filled, formed part extending from the root of said peg toward the gum line.

* * * * *